United States Patent
Linares

(10) Patent No.: US 8,075,506 B2
(45) Date of Patent: Dec. 13, 2011

(54) BODY LIMB CAST INCLUDING AN OUTER RIGID SHELL AND INNER DYNAMIC MEMBERS IN COMBINATION WITH AIR CIRCULATION AND MASSAGE FEATURES

(75) Inventor: Miguel A. Linares, Bloomfield Hills, MI (US)

(73) Assignee: Linares Medical Devices, LLC, Auburn Hills, MI (US), part interest ( * ) Notice: Subject to any disclaimer, the term of this patent is extended or adjusted under 35 U.S.C. 154(b) by 364 days.

(21) Appl. No.: 12/498,469

(22) Filed: Jul. 7, 2009

(65) Prior Publication Data

US 2010/0010408 A1    Jan. 14, 2010

Related U.S. Application Data

(60) Provisional application No. 61/078,865, filed on Jul. 8, 2008.

(51) Int. Cl.
*A61F 13/00* (2006.01)
(52) U.S. Cl. .......................................................... 602/14
(58) Field of Classification Search .................. 602/2, 3, 602/14
See application file for complete search history.

(56) References Cited

U.S. PATENT DOCUMENTS

| | | | |
|---|---|---|---|
| 2,837,088 A | 6/1958 | Moses | |
| 3,307,537 A | 3/1967 | Simon at al. | |
| 3,701,349 A | * 10/1972 | Larson | 602/14 |
| 3,762,406 A | 10/1973 | Wells | |
| 3,908,642 A | 9/1975 | Vinmont | |
| 3,998,220 A | 12/1976 | Cleer, Jr. et al. | |
| 4,308,862 A | 1/1982 | Kalmar | |
| 4,387,710 A | 6/1983 | Beatty, III | |
| 4,898,160 A | 2/1990 | Brownlee | |
| 5,868,690 A | 2/1999 | Eischen, Sr. | |
| 6,053,882 A | 4/2000 | Johansen | |
| 7,229,425 B2 | 6/2007 | Dunagan | |
| 7,250,034 B2 | 7/2007 | Barberio | |
| 7,497,838 B1 | 3/2009 | Dunagan | |
| 2007/0191749 A1 | 8/2007 | Barberio | |

FOREIGN PATENT DOCUMENTS

KR        20050096028 A      10/2005

* cited by examiner

*Primary Examiner* — Kim M Lewis
(74) *Attorney, Agent, or Firm* — Gifford, Krass, Sprinkle, Anderson & Citkowski, P.C.

(57) ABSTRACT

A cast for supporting a limb includes a rigid outer shell, such as provided as first and second assembleable halves interconnected by a plurality of latches. An inner conforming foam insole is supported within the shell and is interconnected by pluralities of linearly extending passageways in combination with radially extending rings and which communicate with additional breathing holes extending through a cross sectional thickness of the insole for introducing an airflow for relieving patient discomfort. A toe attachable fan unit creates the airflow within the insole in communication with a plurality of vents positioned at upper terminating ends of each of the linear extending passageways. A plurality of airbags encircle the insole and are iteratively inflated and deflated to achieve a pulsing massage effect.

15 Claims, 10 Drawing Sheets

BODY LIMB CAST INCLUDING AN OUTER RIGID SHELL AND INNER DYNAMIC MEMBERS IN COMBINATION WITH AIR CIRCULATION AND MASSAGE FEATURES

CROSS-REFERENCE TO RELATED APPLICATIONS

This application claims the benefit of U.S. Provisional Application 61/078,865 filed on Jul. 8, 2008.

FIELD OF THE INVENTION

The present invention relates generally to a body cast, such as for an arm or leg. More specifically, the present invention discloses a cast exhibiting a durable outer shell, inner conforming foam insole and built-in ventilation for both immobilizing and maintaining in comfort a healing limb, while permitting selective access to the cast by authorized medical personnel.

BACKGROUND OF THE INVENTION

The prior art is documented with examples of limb cast designs which incorporate a form of ventilation in order to reduce patient itching and discomfort. Examples of such devices include Dunagan, U.S. Pat. No. 7,229,425, for a method and apparatus for aerating a limb fracture set within a cast and having an array of spaced apart protrusions on an inside surface for facilitating even airflow.

U.S. Pat. No. 3,908,642, to Vinmont, teaches a cast incorporating bladders with vents for receiving and venting exteriorly delivered pulses of air. Johansen, U.S. Pat. No. 6,053,882, teaches a cast ventilation sleeve exhibiting an elongated flexible bag positioned between the cast and the wearer's skin, and within one side of which pressurized air aerates the cast. Other venting and aeration type devices include, among others, such as those set forth in Dunagan, U.S. Pat. No. 7,479,838 and Barberio, U.S. Pat. No. 7,250,034.

SUMMARY OF THE INVENTION

The present invention discloses an improved body limb cast for both supporting an injured limb as well as providing a combination of air flow ventilation and pulsating relief to inevitable patient discomfort, such as itching, and which is associated with protracted periods of time during which the cast must be worn. The cast includes a rigid outer shell, such as provided as first and second assembleable halves which, upon assembly, are interconnected by a plurality of latches.

An inner conforming foam insole is supported within the shell. A network of interconnecting passageways defined within the insole includes pluralities of linearly extending passageways in combination with radially extending rings, these communicating with additional breathing holes extending through a cross sectional thickness of the insole for introducing an airflow for relieving patient discomfort.

A toe attachable fan unit can be communicated with such as a separate power supply for creating an airflow within the insole which is in communication with a plurality of vents positioned at upper terminating ends of each of the linear extending passageways. A plurality of airbags can also encircle the insole and which are iteratively inflated and deflated to achieve a pulsing massage effect.

BRIEF DESCRIPTION OF THE DRAWINGS

Reference will now be made to the attached drawings, when read in combination with the following detailed description, wherein like reference numerals refer to like parts throughout the several views, and in which.

DETAILED DESCRIPTION OF THE PREFERRED EMBODIMENTS

As discussed previously, the present inventions discloses a cast exhibiting a durable outer shell, inner conforming foam insole and built-in ventilation for both immobilizing and maintaining in comfort a healing limb, while permitting selective access to the cast by authorized medical personnel. The cast, as will be described below, is an improvement over prior art ventilating cast designs in that it incorporates more features into a compact and portable design and additionally provides such advantages as keyed/limited access to such as authorized medical personnel as well as an optional massage function which assists in retaining/restoring blood flow throughout the limb, this such as further to avoid the necessity of administering blood thinner drugs and which is often required in instances of inadequate blood flow and/or immobility of the patient.

Figure 1:
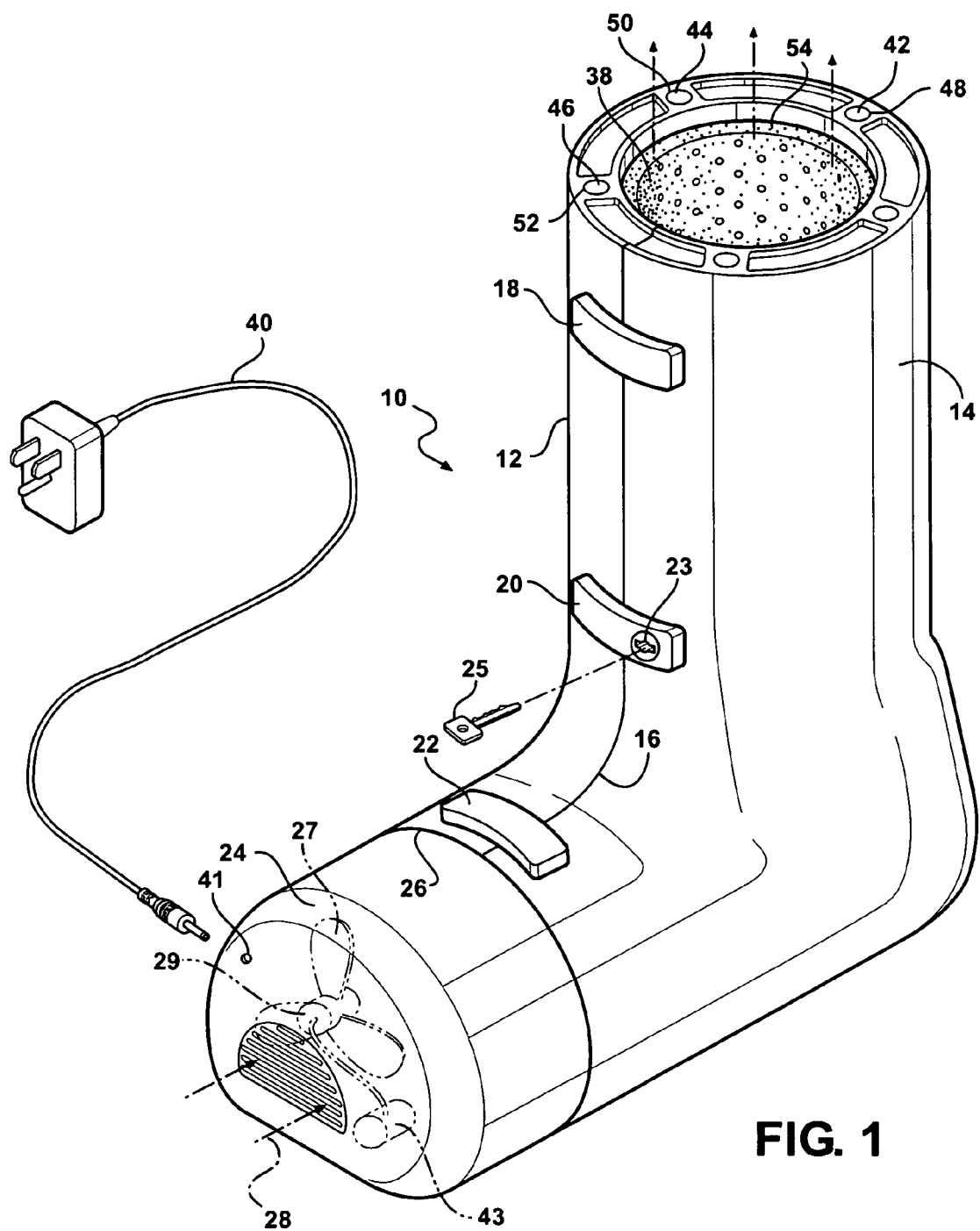
FIG. 1 is a perspective view of a ventilating body limb cast according to a preferred embodiment of the present inventions.

Referring first to FIG. 1, a perspective view is shown at 10 of a ventilating body limb cast according to a preferred embodiment of the present inventions. A rigid outer shell, such as constructed of a durable polymeric or other material exhibiting the necessary properties of rigidity and impact resistance includes, in one possible embodiment, a first half 12 and a second half 14 each of which exhibits aligning inner edge profiles which assemble together along mating line 16 about a wearer's injured limb, such as any of a foot, ankle or lower leg.

Figure 8:
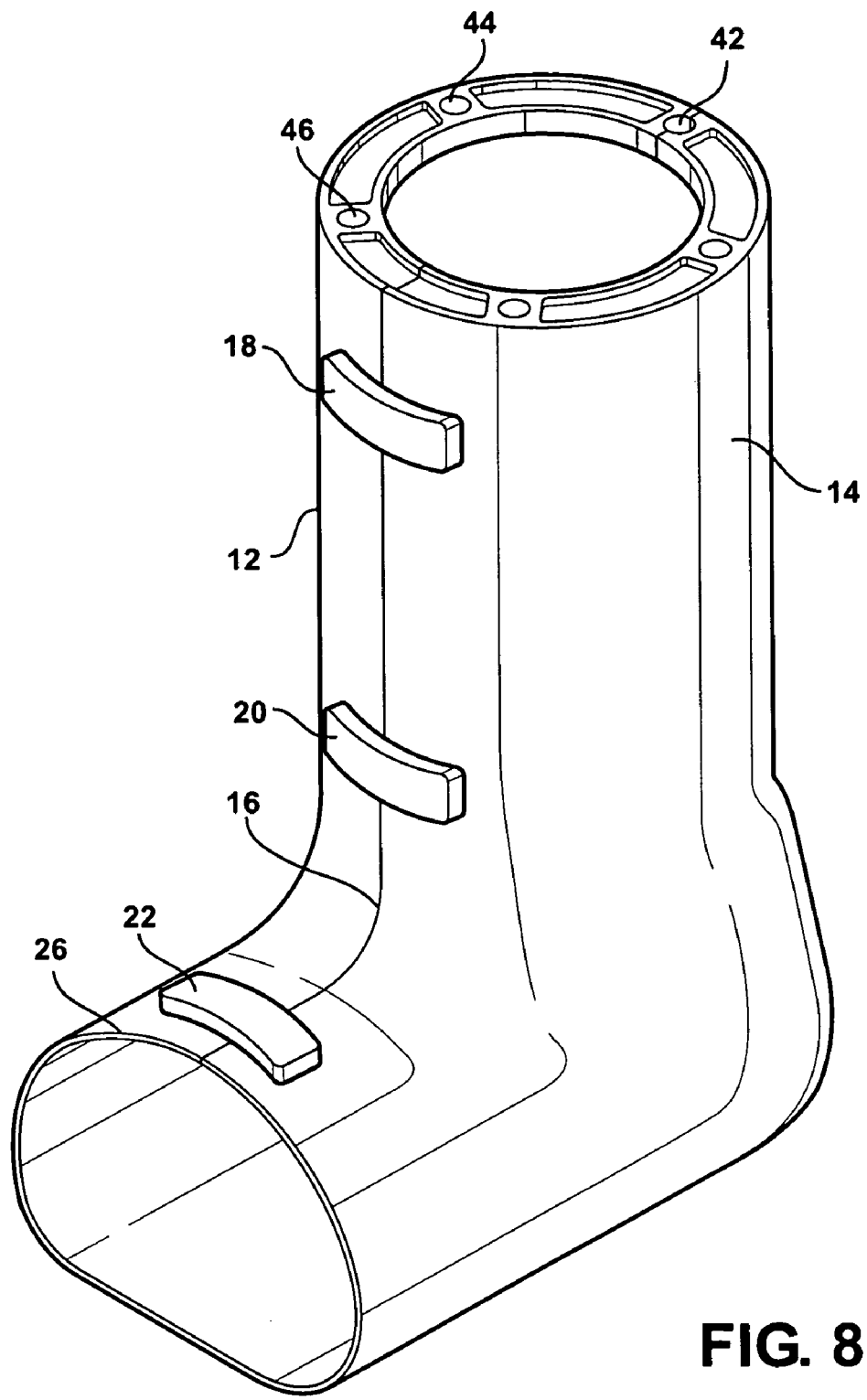
FIG. 8 is a further perspective view of the cast shell.

The outer shells halves 12 and 14 can also be provided as separate halves (and in which an additional mating line extends in parallel along a rear surface) or the halves can be integrally formed (as better shown in sectional perspective of FIG. 8) along a rear edge, and so that the outer shell is capable of being deformably manipulated to clamshell assemble over the patient's limb, subsequent to which the halves are aligned along the mating line 16. The cast is shown in the illustrated embodiment as a foot/lower leg boot shaped cast, however which is also understood that the cast design of the present invention can be reshaped or otherwise reconfigured so that it equally applies to any of a lower/upper leg, arm, torso, neck or like area in which the advantages associated with the current design are applicable. It is further envisioned that the cast can exhibit an adequately deformable consistency, such as with a living hinge construction, and further be provided as a single piece with a single lengthwise incised location such that the interconnected portions can be separated along such a lengthwise extending and incised edge and subsequently deformably installed about the limb.

As will be described in additional detail throughout the succeeding views, additional features associated with the body cast 10 include a plurality of individual latch portions 18, 20, 22, these being mounted to one selected halve 12 or 14 and engageable with the other half 12 or 14. The latch portions 18-22 can include any type of pivoting clasp and catch mechanism (hidden from view) as is known and is also understood to each optionally include a key entry feature (see access slot 23 in selected latch 20 for receiving key 25) for selectively locking inter-engaging such as tab and slot locations (or other catch portions) established between the latches and their associated engaging locations opposite their pivoting supported locations, this in order to provide exclusive unlocking access of the rigid shell only to authorized medical personnel.

Upon assembling and aligning the first and second halves 12 and 14, the latches 18-22 are manipulated along their secured half (either 12 or 14), across the mating line 16, in order to engage the latch to a location associated with the other half (12 or 14). Although not shown, it is envisioned that the outer halves 12 and 14 can be pivotally connected or otherwise aligned along opposite rear edges relative to the latches 18-22. It is also envisioned that additional latches can be likewise provided along such an opposite rear edge of the outer boot.

Figure 2:
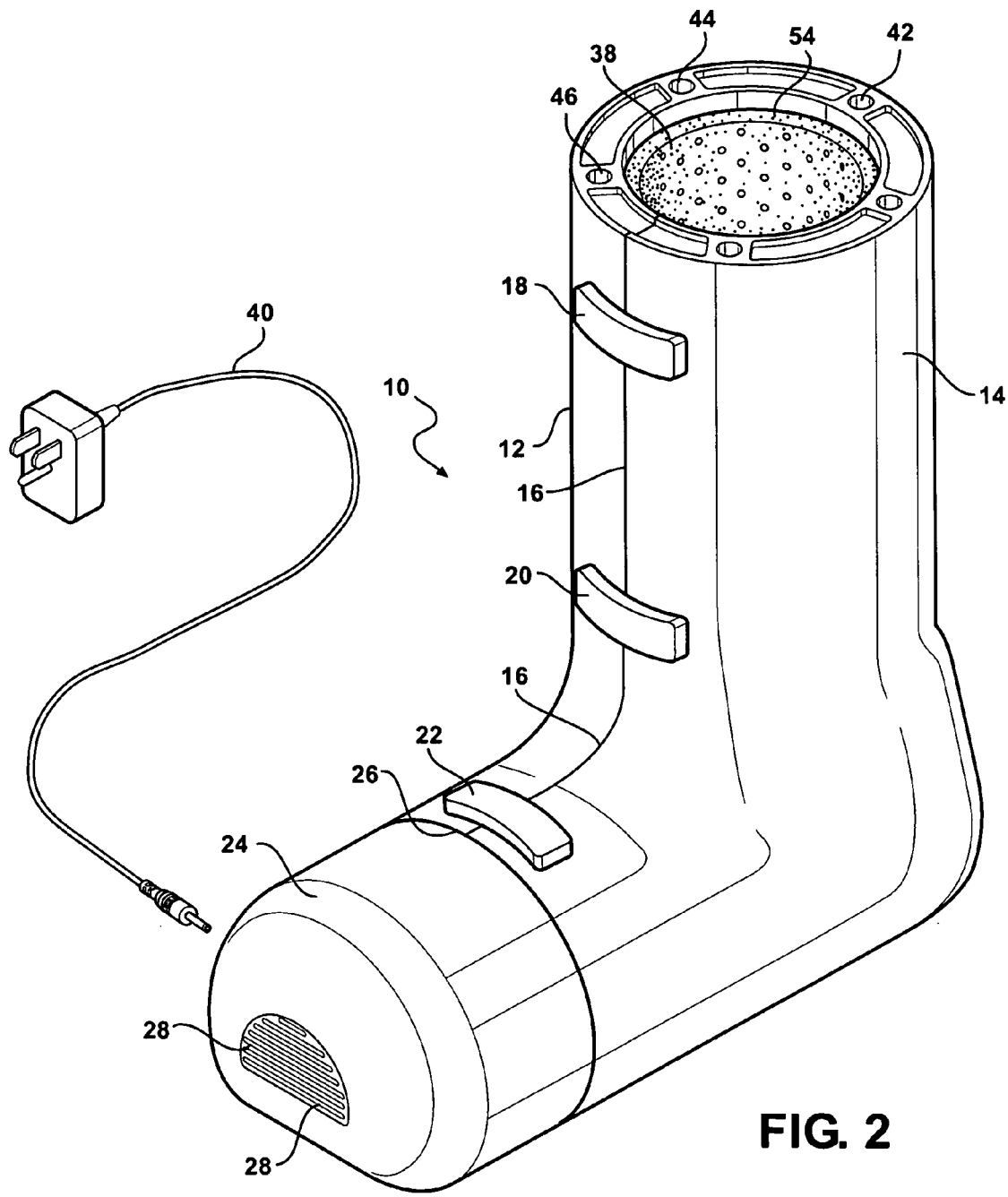
FIG. 2 is an illustration similar to that shown in FIG. 1 and in particular referencing a forward positioned and powered/rechargeable toe unit for operating the assembly.
Figure 3:
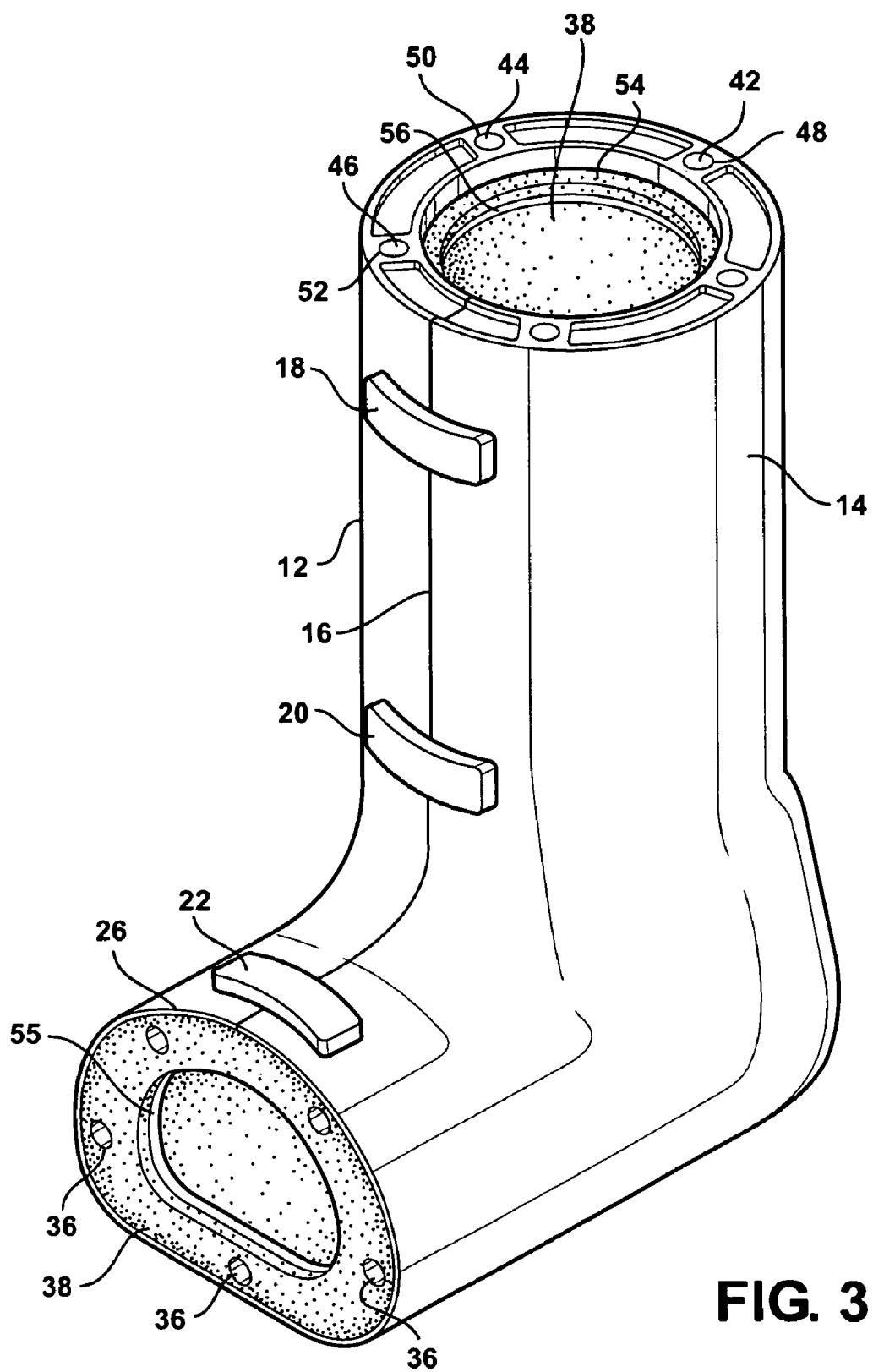
FIG. 3 is a sectional perspective of an outer shell component constructed of assembleable halves associated with the body cast and highlighting keyed entry latches for permitting removal of the cast by a doctor or other authorized medical professional.

A toe located, ergonomically configured and end supported/assembleable powered/fan unit is shown at 24 (also termed a bag pump unit) and is secured to a forward open location defined by the assembled outer shell halves 12 and 14 (see as shown by open toe end 26 in each of FIGS. 1-3). The unit 24, as shown in each of FIGS. 1, 2 and 9, exhibits such as a plasticized outer construction which houses an interior supported and portable driven fan unit (see in phantom at 27 in FIG. 1) built into a forward most location of the unit 24 and so that the fan 27 does not interfere with the placement of the wearer's foot and toes within the boot cast 10. A plurality of ventilation grates or slots are defined, at 28, for admitting air into the unit when the fan is activated. Other features, such as a miniaturized electric motor 29 is also shown in FIG. 1 for driving the fan 27.

Engagement projections are illustrated at 30, 32 and 34 (see sectional perspective of FIG. 9) in circumferential spaced and projecting fashion around an end face perimeter of the unit 24 and, during assembly of the unit 24 to the open toe location of the outer shell, aligns and engage with a mating array of apertures (at 36 et. seq. in FIG. 3) defined in a three dimensional shaped and interiorly hollowed foam insole portion 38 which is cushioning, structurally supporting and generally smaller in dimension for seating within the defined interior of the outer shell halves 12 and 14, in generally matching fashion in configuration the outer assembled shell. As will be subsequently described in more detail, the fan unit 24 generates an air flow which is employed in either a ventilation (this such as to reduce the effects of itching) or closed/pressurized mode of operation (e.g. massage) in use with associated features incorporated into the foam insole portion 38.

The engagement projections 30-34 can also exhibit air pressure delivery nozzles for admitting air pressurized by the fan into the communicating apertures 36, a more complete explanation of which being provided with reference to FIGS. 4-6, 10 and 11. The portable fan unit 24 further includes a plug in rechargeable adapter, see at 40, which accesses an inlet recharge delivery location (at 41) associated with the toe attachable fan unit 41 and, upon plugging into an existing wall outlet location, can operate the fan unit individually and/or can recharge a separate and communicating portable battery 43 associated with the fan unit 24 to be iteratively recharged for ongoing operation.

Referring again to FIGS. 1-3, the air generated by the toe attached fan 24, after being communicated through the apertures 36 in the insole portion 38, are discharged through upper end located vents 42, 44, 46, et, seq, and as illustrated by an inwardly radially projecting top rim associated with the halves 12 and 14 of the rigid cast shell which overlaps the upper communicating edge of the foam insole/insert 38. As best shown in the enlarged top view of FIG. 5, the upper end located vents, again 42-46, et. seq., each further include push tab openable/closable vent stop 48, 50, 52, et seq. incorporated into each vent and capable of each being displaced between a projecting/open position (see vent stops 48 and 50) and a depressed/closed position (see vent stop 52). The push tab vent stops 48-52 can each further include such as spring loaded portions combined with an appropriate tab and slot configuration and in order to selectively open and close each tab stop. As will be described, the ability to open or close the upper end vents enables the cast to operate in either of an open airflow circulation/ventilation mode or, alternatively, in a closed/pressurized massage or pulse mode.

Figure 4:
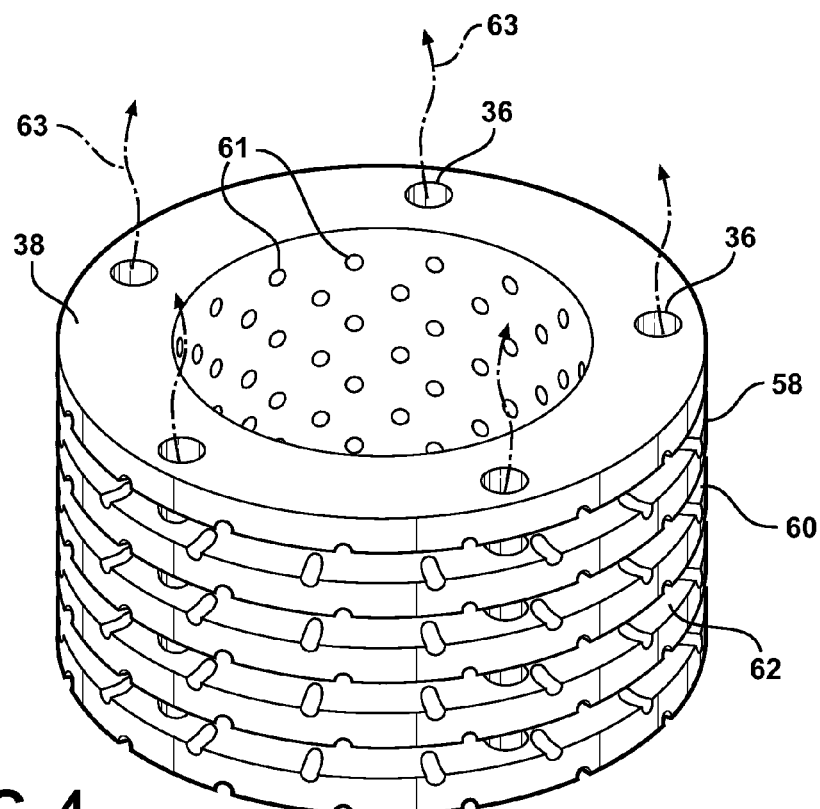
FIG. 4 is a sectional illustration of a foam insole supported inside of the outer shell component and exhibiting both linearly and radially intersecting and communicating ventilation passages through which a conditioned airflow is passed in contact with a wearer's skin.
Figure 5:
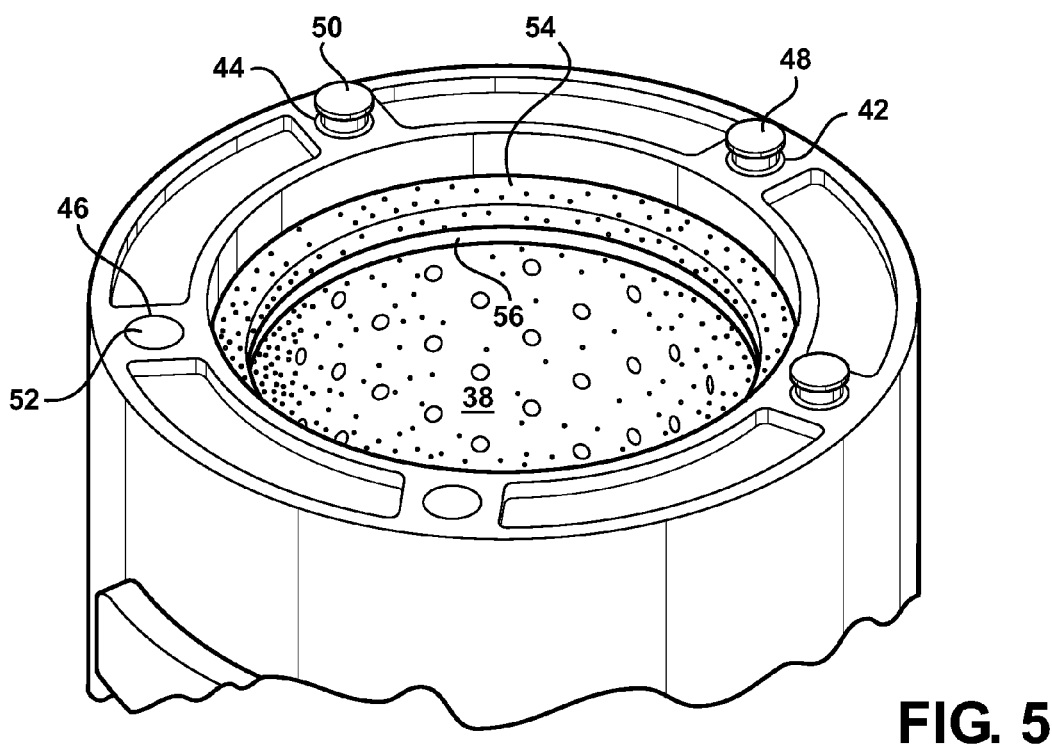
FIG. 5 is an enlarged top view of the outer shell component shown in FIG. 3 and further illustrating the selectively openable/closable vent stops associated with the ventilation passages and which, upon closing, enable activation of a massage mode.

Referring to FIG. 4, a sectional illustration of a portion of the foam insole 38 is shown supported inside of the outer shell component (e.g. such as defined by halves 12 and 14). The insole 38 can be constructed of any sponge-like material and, in one variant, exhibits a fairly consistent construction between a first location proximate the open toe end 26 of the outer shell and a second opposite end location associated with the top ventilation discharge (see upper insole end 54 in each of FIGS. 1-3, 5-7 and 10-12). An annular and inwardly extending seal 56 (see as best shown in FIG. 5) is also provided approximate the upper end 54 of the foam insole 38 (whereas an identical seal 55 is located proximate the bottom toe unit end of the insole in FIG. 3), this operating in specific, such as massage, modes in order to maintain air pressure induced massage along varying interior locations of the foam insole 38 in contact with the wearer's skin.

Referring again to FIG. 4, the foam constructed insole 38 is again shown includes a combination of interconnected passageways, these consisting of 1) the linear extending and spaced apart apertures collectively shown at 36 in FIG. 3 which are embedded within the insole 38 (these again extending between the toe and upper boot ends of the cast; 2) spaced apart and outer surface defined recess rings 58, 60, 62, et. seq., which communicate in a peripheral or circumferential extending fashion with the linear extending apertures 36; and 3) a further (large) plurality of smaller sized radially extending holes 61 which extend radially through a thickness of the cross sectional ring shape associated with the insole 38, between the user's skin and the exterior radius of the insole 38 in communication with the spaced apart linear passageways 36 and the interconnecting outer surface recess rings 58-62 as further shown and in order to substantially ventilate the entire insole 38.

Figure 10:
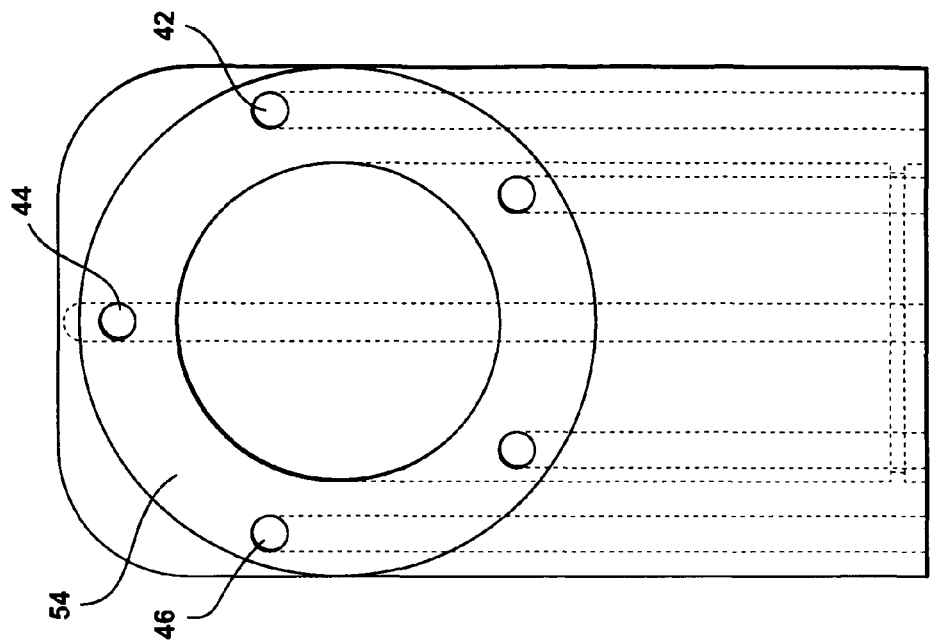
FIG. 10 is a top phantom view of the outer boot shell and illustrating the conduit passageways for communicating either a ventilated or closed massage airflow throughout the additional ventilation passages defined in the foam insole.
Figure 11:
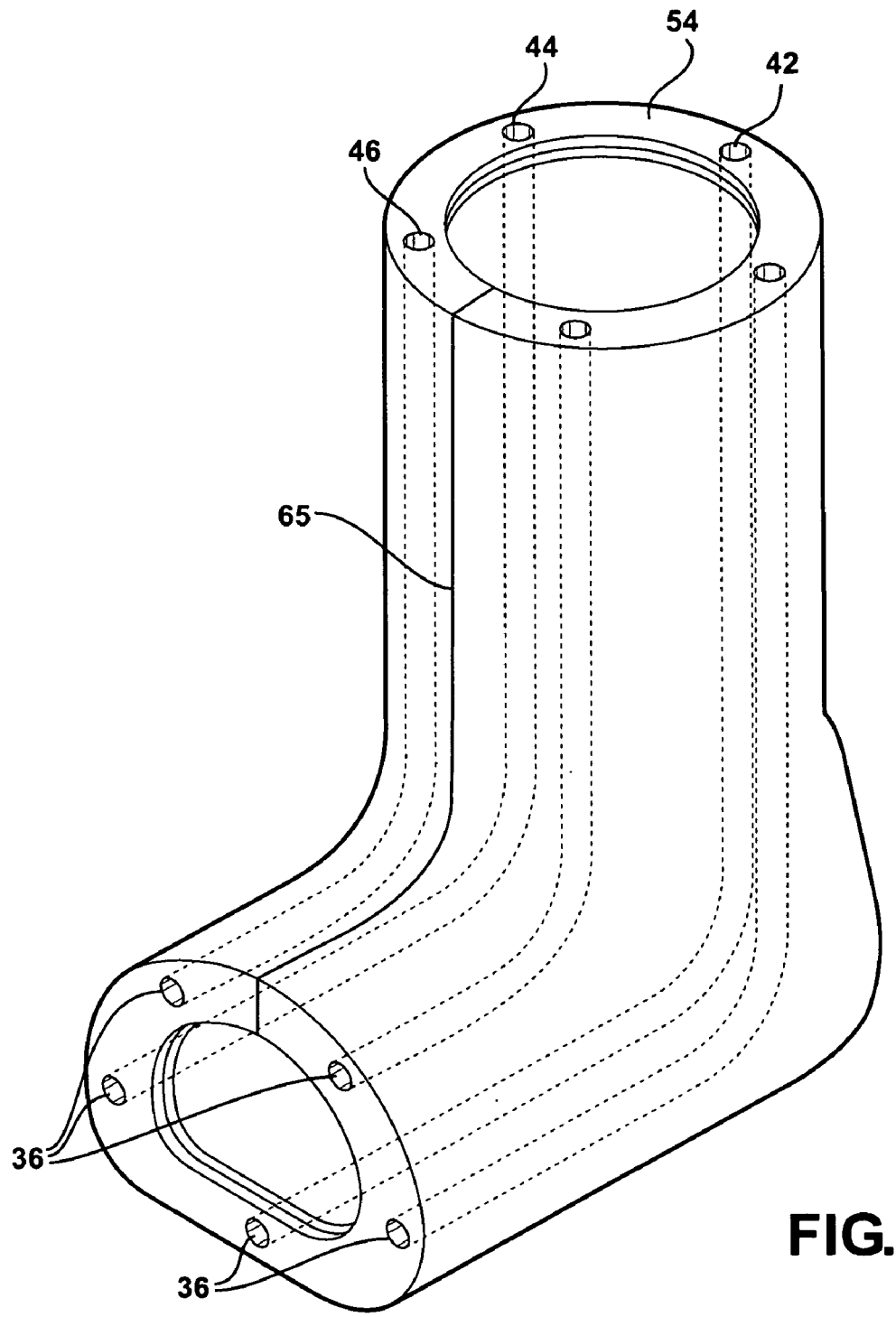
FIG. 11 is a perspective view of the outer boot shell shown in FIG. 10.

In this fashion, the air adjoining the surface of the wearer's skin is heated and subsequently withdrawn through the radially extending holes 61, communicated to the rings 58-62, and expelled through the apertures 36 communicating with the rings and terminating at locations 42, 44 and 46 associated with the top end 54 of the insole 38 (see also directional airflow arrows 63 in FIG. 4) and the inwardly radially extending and overlapping top edges of the rigid cast with which the upper end vents 42, 44, 46, et seq. and associated vent stops 48, 50, 52 et. seq. align. FIGS. 10 and 11 further illustrate in phantom the arrangement of the interior defined and linear extending passageways 36 associated with the foam insert 38, it being understood that the additional variants of the present inventions can operate with or without the provision of the communicating rings and smaller sized radial extending air holes, this depending upon the degree of communicating ventilation which can be afforded through the foam insole, and such as via air delivered through the linear passageways.

Additional to the operational parameters of the fan 24, it is understood that the cool air from the toe vent inlets 36 naturally flows up through the foam insole 38 as the air is heated, and then exhausting the same out the calf area vents 42-46, et seq. In this fashion, the cast can operate in given applications without the need of the attachable fan unit 24. Alternatively, the fan unit 24 can be activated to also assist, to some degree, in the generation of ventilation airflow, as well as in the pulse/massage modes Referring now to FIG. 6, a sectional perspective of a foam insole insert is again shown at 38, and which is use is installed inside of the outer durable shell. The foam insole may include an incised forward edge, see at 65 (also shown in the related variant of FIG. 11), extending between the top and bottom ends of the foam insert 38 and in order to form fit or otherwise apply or fashion the same around the injured foot, ankle or lower leg of the wearer prior to assembly of the outer two piece rigid shell halves 12 and 14.

A plurality of individually configured and outer surface positioned airbags 64, 66, 68 and 70 are also shown and are located in slightly spaced apart fashion between the lower toe end and upper calf end. The airbags 64-70 each define a bladder portion which, upon expanding creates an annular air pocket, the pockets being interconnected via a communication line 72 extending consecutively to each of the airbags and which is fed from the pump unit 24 at an inlet feed end.

Figure 9:
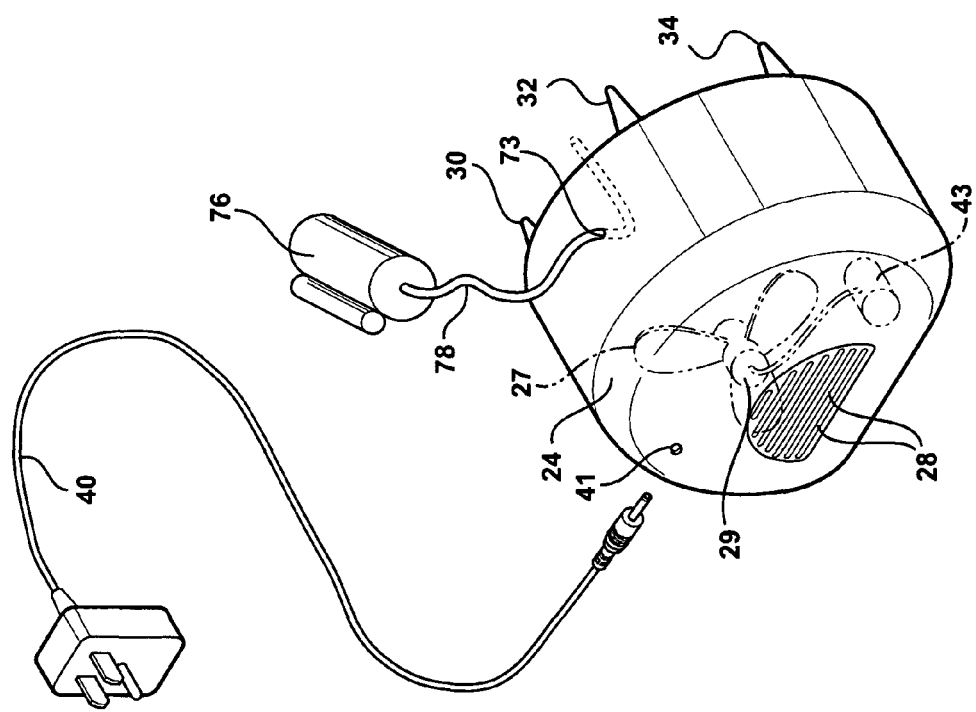
FIG. 9 is a sectional perspective of the toe positioned fan unit.

In order to establish a necessary degree of pressurization through the line 72, for selectively/successively inflating the individual airbags, any suitable type of alternative structure cam be incorporated either directly into the portable fan unit 27 or otherwise provided separately and communicated via the fan unit through a separate airflow line extending through the unit, see at 73 in FIG. 9, for providing the necessary pressurization for inflating/deflating the bladder designed airbags 64-70, such as beyond the typical capabilities of the built in ventilating fan unit 27. Such exterior attachable pressurizing structure can include a portable compressor/pump 76 (in FIG. 9) or the like which is communicated to the toe unit airflow inlet 73 via such as a further conduit 78

Although not shown, it is understood that the airbags 64-70 can be iteratively/successively pressurized by the communication line 72 (and such as is fed with pressurized air via the activation of the fan unit 24 to which it is connected). Following closing of the upper end air vents (see vent stops 48-52 in FIG. 5), inflation of the airbags 64-70 (e.g. such as sequentially) causes the underlying sections of the foam insole 38 (e.g. those around which a selected airbag is wrapped) to inwardly pressurize (further due to the constriction of the outer positioned shell) against the surface of the wearer's limb encased within the cast, and in order to create a pulsing/massaging effect upon the wearer.

Although not shown, it is also understood that additional variants can include the foam insole (aside from being shown as a unitary extending element 38) being broken into individually positioned and consecutive sections, each of which is encased within a separate bladder constructed airbag and supported inside of the outer assembled shell. In this fashion, the airbags are inflated and subsequently deflated in sequence, thereby applying inwardly directed pressure from the toes, through the ankle and the lower calf of the user, this creating a massaging effect which promotes blood flow to the user's limb.

By repeating the inflation/deflation protocol, as dictated by an internal processor control mechanism associated with the fan unit 24, operation of a massage mode is enabled and which can assist in limiting or avoiding the necessity of administering blood thinning/anti-clotting drugs to the user. It is also understood that the features of the body cast can operate with either or both the provision of the ventilation air passageways (this reducing patient itching of the skin surface) and/or the massage/pulse inducing airbags (again promoting blood flow).

Figure 7:
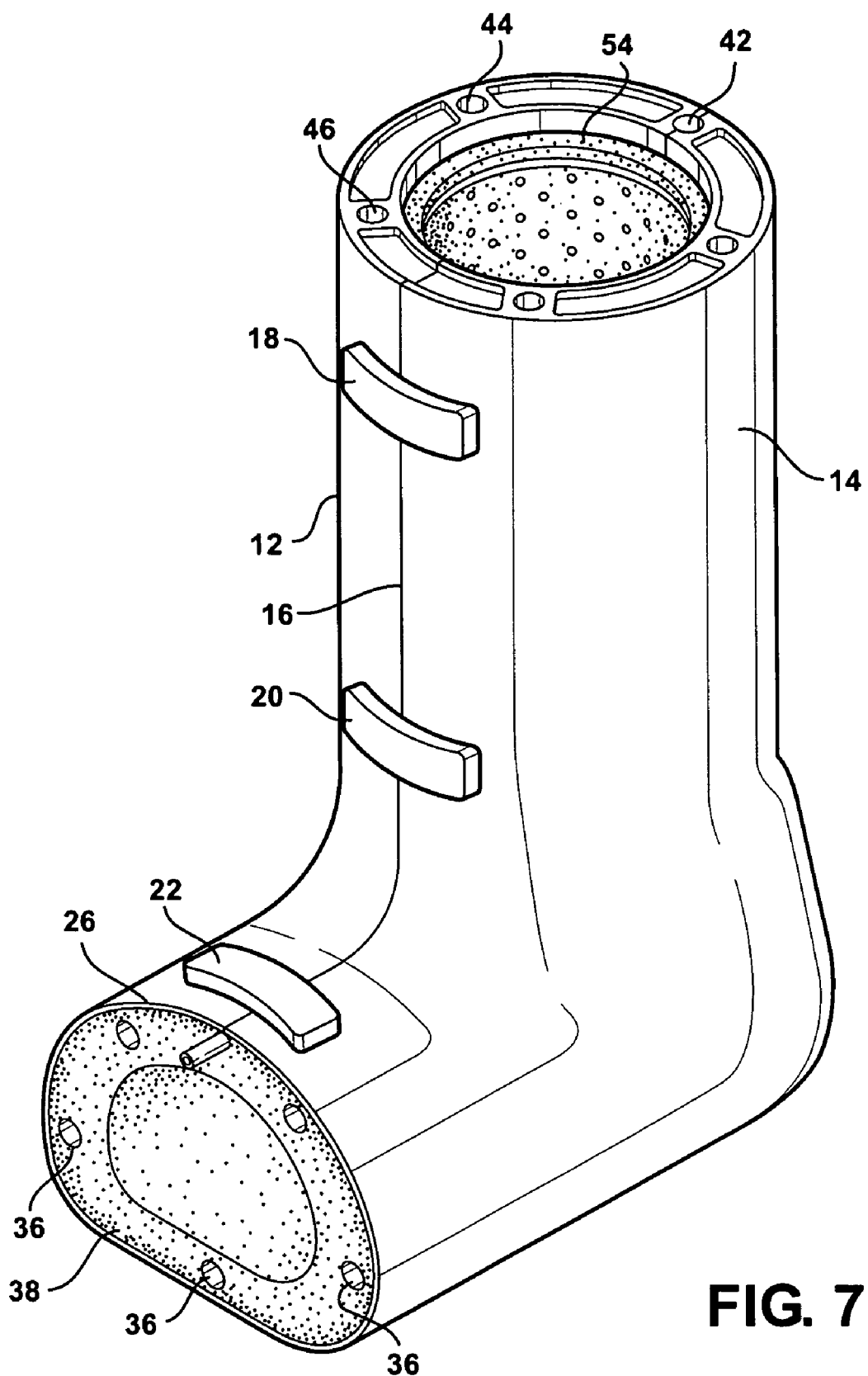
FIG. 7 is an illustration similar to that shown in FIG. 1 and in which the powered toe unit is removed to expose the spongy/closed cell foam positioned at a proximate forward foot location of the cast.

Referring now to FIG. 7, an illustration similar to that shown in FIG. 1 is presented and in which the powered toe unit 24 is removed to expose the spongy/closed cell foam unit positioned at a proximate forward foot location of the cast. The consistency of the foam insole 38 is understood to include any type of natural or synthetic sponge-like material, this providing the ability to contour to the surface of the user's limb, to communicate ventilated airflow throughout the interconnecting passages in the insert, as well as the ability to selectively inflate/deflate according to the massage mode described herein.

Figure 6:
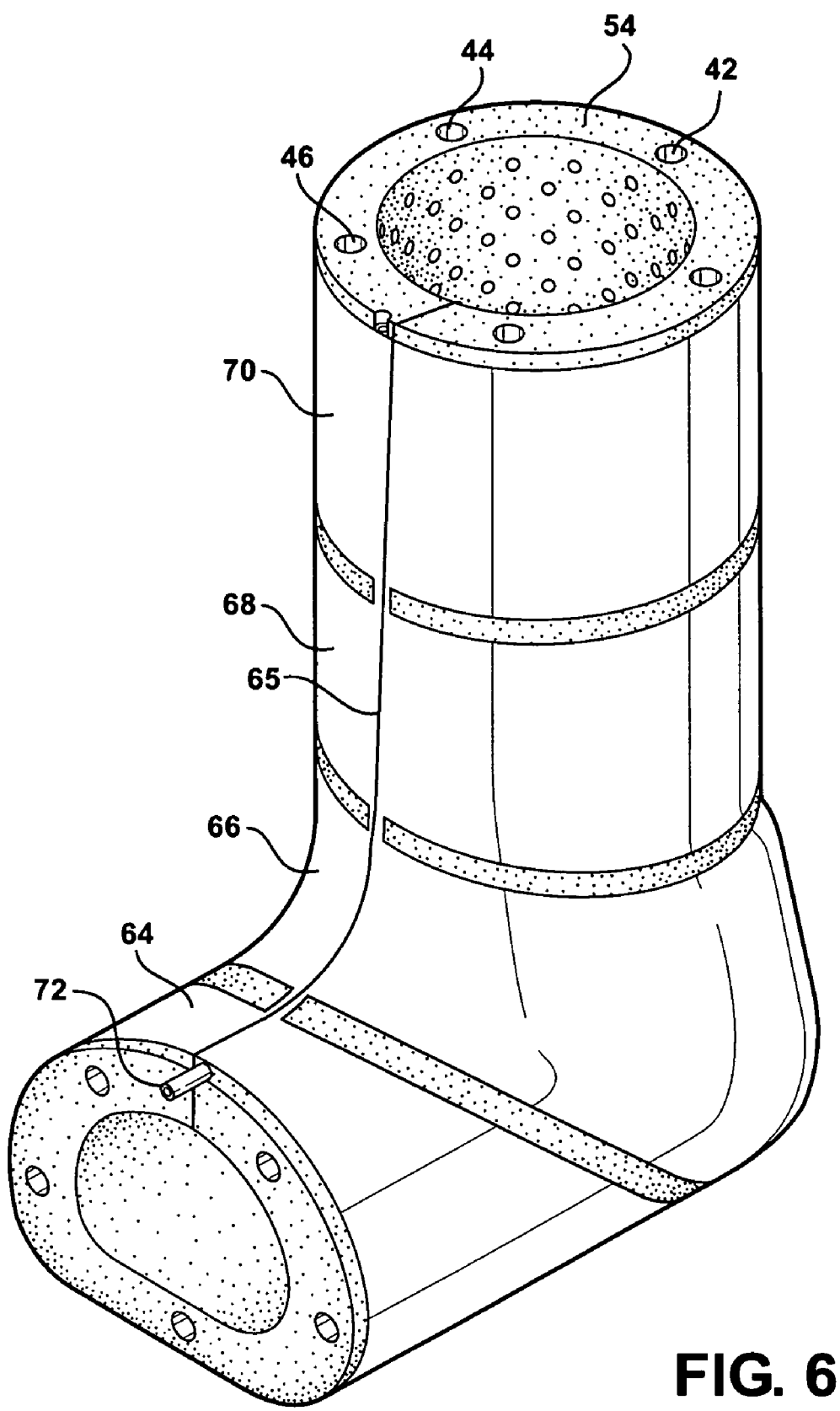
FIG. 6 is a sectional perspective of the foam insert, installed in use inside of the outer durable shell, and better showing the features of the individual interconnected and successively inflatable bag sections associated with the massage protocol, this avoiding the necessity of administering blood thinners to a patient during massage therapy.
Figure 12:
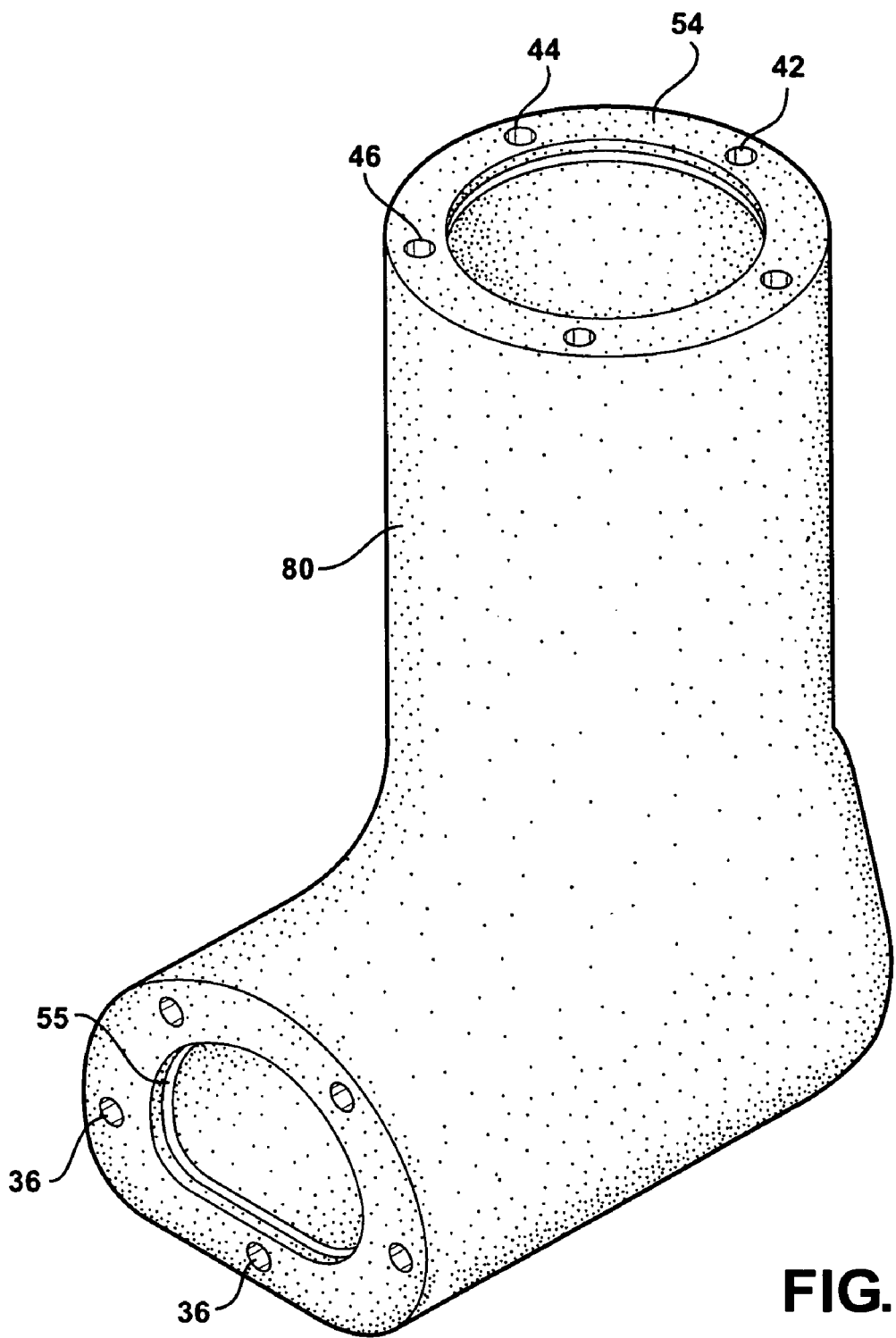
FIG. 12 is a further perspective view of a foam insole, similar to that shown in FIG. 6, and illustrating the foam insole without the provision of the individual encircling air bags or bladders.

Referring finally to FIG. 12, a further perspective view is shown of another version 80 a foam insole insert portion, this similar to that shown in FIG. 6 and illustrating the foam insole without the provision of the individual encircling air bags/bladders or of the linearly extending incised edge. Depending upon the elasticity associated with the insole 80, and/or the severity and location of the patient injury, it is contemplated that the insole insert can be deformably manipulated to position about the lower leg, ankle and foot of the user's injured limb (such as without the requirement of the incised edge shown at 65). It is also envisioned and understood that the insert and outer shell can be combined into a single unit, whether as one deformable piece with an incised linear edge or as first and second separable and assembleable halves utilizing latches, clasps or the like.

Having described my invention, other and additional embodiments will become apparent to those skilled in the art to which it pertains, and without deviating from the scope of the appended claims:

I claim:

1. An aerating cast for supporting a limb, comprising:
   an outer shell;
   a cushioning insert supported within said shell; and
   a plurality of linearly extending passageways defined within said insert, at least one of a further plurality of exterior surface positioned recess rings defined in said insert and an additional plurality of radially extending breathing holes extending through a cross sectional thickness of said insert and communicating with said outer shell in order to introduce an airflow into said insert to relieve patient discomfort.

2. A cast for supporting a wearer's limb, comprising:
   an outer shell;
   an insert supported within said shell and incorporating a network of interconnecting passageways extending in any of linear, peripheral and radial directions and in communication with a surface of the wearer's limb; and
   a toe attachable unit secured over an open lower end of said shell and insert and for generating an airflow for communication through said passageways.

3. The cast as described in claim 2, wherein said insert further comprises a plurality of individual and inflatable air bladders.

4. The cast as described in claim 3, further comprising a pressurized air flow line extending from said toe unit to said insert in communication with said air bladders.

5. The cast as described in claim 4, further comprising a plurality of vents incorporated into an upper end and annularly inward projecting portion associated with said shell and which is positioned at an upper terminating end of each of linear extending passageways defined in said insert, each of said vents further comprising an openable/closable push tab.

6. The cast as described in claim 2, wherein said outer shell further comprises first and second assembleable halves, a plurality of latches supported upon said rigid shell and extending across a mating line associated with first and second halves.

7. The cast as described in claim 2, wherein said unit further comprises a fan unit built into a forward most location, a plurality of ventilation grates or slots defined along a forward edge of said unit for admitting air upon activation of said fan.

8. The cast as described in claim 2, wherein said unit further comprises a miniaturized electric motor for driving said fan and a portable battery, a plug in rechargeable adapter accessing an inlet recharge delivery location associated with said unit.

9. An aerating cast for supporting a limb, comprising:
   an outer shell;
   a cushioning insert supported within said shell;
   a plurality of linearly extending passageways defined within said insert and communicating with said outer shell by way of a plurality of vents incorporated into an upper end and annularly inward projecting portion associated with said shell and which is positioned at an upper terminating end of each of said linear extending passageways defined in said insert in order to introduce an airflow into said insert to relieve patient discomfort.

10. The cast as described in claim 9, each of said vents further comprising an openable/closable push tab.

11. The cast as described in claim 10, wherein said insert further comprises a plurality of outer positioned airbags which are iteratively inflated and deflated to achieve a pulsing massage effect upon closing said vent tabs.

12. An aerating cast for supporting a limb, comprising:
    an outer shell;
    a cushioning insert supported within said shell; and
    a plurality of passageways defined within said insert and communicating with said outer shell via a toe attachable fan unit including a plurality of ventilation grates defined along a forward edge thereof for admitting air upon activation of said fan and for creating and introducing an airflow into said insert to relieve patient discomfort.

13. The cast as described in claim 12, wherein said unit further comprises a miniaturized electric motor for driving said fan and a portable battery.

14. The cast as described in claim 12, wherein said unit further comprises engagement projections extending in circumferential spaced and projecting fashion around an end face perimeter for assembly with an open toe location of said outer shell.

15. The cast as described in claim 12, wherein said unit further comprises a plug in rechargeable adapter which accesses an inlet recharge delivery location associated with said unit.

* * * * *